(12) United States Patent
Monsaert et al.

(10) Patent No.: US 9,278,345 B2
(45) Date of Patent: Mar. 8, 2016

(54) PROCESS FOR PREPARATION OF RUTHENIUM-BASED CARBENE CATALYSTS WITH CHELATING ALKYLIDENE LIGANDS

(75) Inventors: Stijn Frans Monsaert, Zottegem (BE); Francis Walter Cornelius Verpoort, Oekene (BE)

(73) Assignee: UMICORE AG & CO. KG, Hanau-Wolfgang (DE)

( * ) Notice: Subject to any disclaimer, the term of this patent is extended or adjusted under 35 U.S.C. 154(b) by 337 days.

(21) Appl. No.: 13/521,969

(22) PCT Filed: Jan. 25, 2011

(86) PCT No.: PCT/EP2011/000300
§ 371 (c)(1),
(2), (4) Date: Oct. 12, 2012

(87) PCT Pub. No.: WO2011/091980
PCT Pub. Date: Aug. 4, 2011

(65) Prior Publication Data
US 2013/0035494 A1    Feb. 7, 2013

(30) Foreign Application Priority Data

Jan. 29, 2010 (EP) .................................. 10000928

(51) Int. Cl.
*C07F 15/00* (2006.01)
*B01J 31/22* (2006.01)
*B01J 31/24* (2006.01)

(52) U.S. Cl.
CPC .......... *B01J 31/2204* (2013.01); *B01J 31/2265* (2013.01); *B01J 31/24* (2013.01); *C07F 15/0046* (2013.01); *B01J 2231/543* (2013.01); *B01J 2531/821* (2013.01)

(58) Field of Classification Search
CPC .................................................. C07F 15/0046
See application file for complete search history.

(56) References Cited

U.S. PATENT DOCUMENTS

| | | | |
|---|---|---|---|
| 4,717,785 | A | 1/1988 | Paxson |
| 5,773,665 | A | 6/1998 | Silverman et al. |
| 7,026,495 | B1 | 4/2006 | Pederson |
| 7,435,858 | B2 | 10/2008 | Van Kruchten |
| 2003/0166955 | A1 | 9/2003 | Pederson |
| 2006/0122412 | A1 | 6/2006 | Pederson |
| 2008/0108841 | A1 | 5/2008 | Pederson |
| 2009/0088581 | A1 | 4/2009 | Pederson |

FOREIGN PATENT DOCUMENTS

| | | |
|---|---|---|
| WO | 02/14376 A2 | 2/2002 |
| WO | 2003/044060 A2 | 5/2003 |
| WO | WO 03/044060 A2 * | 5/2003 |
| WO | 2004/035596 A1 | 4/2004 |
| WO | 2004/112951 A | 12/2004 |
| WO | 2008/034552 A1 | 3/2008 |

OTHER PUBLICATIONS

Rohm and Haas "AMBERLYST 15WET Industrial Grade Strongly Acidic Catalyst for Catalysis and Separation technologies" 2003, the whole document.*
Randl, S., et al.:"Highly Selective Cross Metathesis with Acrylonitrile Using a Phosphine Free Ru-Complex", Synlett, Georg Thieme Verlag, DE, No. 3, Jan. 1, 2001, pp. 430-432, XP002906693.
International Search Report and Written Opinion dated May 17, 2011 from PCT/EP2011/000300.
S. B. Garber, J. S. Kingsbury, B. L. Gray, A. H. Hoveyda, J. Amer. Chem. Soc. 2000, 122, 8168-8179.
D. Burtscher, C. Lexer et al, J. of Polymer Science, Part A: Polymer Chemistry 2008, vol. 46, 4630-4635.
S. Gessler, S. Randl and S. Blechert, Tetrahedron Letters, 2000, 41, 9973-9976.
A. Fuerstner, P. W. Davies and C. W. Lehmann, Organometallics, 2005, 24, 4065-4071.
M. Bieniek, A. Michrowska, L. Gulajski and K. Grela, Organometallics, 2007, 26, 1096-1099.
M. Barbasievicz et al., Organometallics, 2006, 25, 3599-3604.
J. Am. Chem. Soc. 2005, vol. 127, 15265-15272, Mark Gandelman.
J. Am. Chem. Soc. 2000, vol. 122, 6601-6609, David M. Lynn.
J. Am. Chem. Soc. 2001, vol. 123, 5372-5373, Mark Gandelman.
Rohm and Haas Company, Catalyses Lab Guide, Jun. 2004.
Rohm and Haas, 2006, Amberlyst.
Varian, Inc., 2003, Solution Phase Syntheis.
A. Falchi et al—PEG-dichlorotriazine . . . —Organic Letters 2000, vol. 2, No. 22, 3429-3431 —cited by JPO.
D. L. Flynn et al—Chemical Library Purfication Strategies . . . — J.Am.Chem. Soc. 1997, 119, 4874-4881—cited by JPO.

* cited by examiner

*Primary Examiner* — Joseph Kosack
(74) *Attorney, Agent, or Firm* — Levin Santalone LLP; John Santalone

(57) ABSTRACT

The invention relates to a method for preparation of ruthenium-based carbene catalysts with chelating alkylidene ligands (so-called "Hoveyda-type catalysts") in a cross metathesis reaction by reacting a ruthenium-alkylidene complex with an olefin derivate in the presence of a polymer-supported cation-exchange resin (PSR) acting as a ligand (i.e. phosphine or amine) scavenger. Preferably, penta-coordinated ruthenium benzylidene or indenylidene carbene complexes are employed. The polymer-supported cation-exchange resin (PSR) may be an acidic resin (comprising sulfonic acid or carboxylic groups) or a resin containing carboxylic acid chloride (—COCl) groups or sulfonyl chloride (—$SO_2$Cl) groups. The process is versatile and environmentally friendly; high yields are obtained.

14 Claims, 1 Drawing Sheet

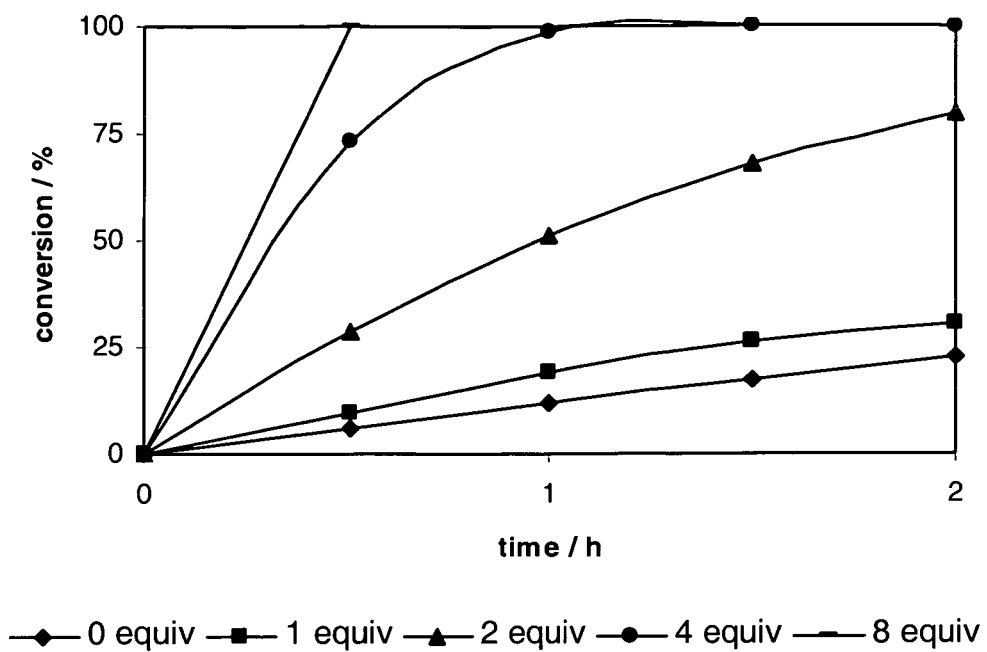

PROCESS FOR PREPARATION OF RUTHENIUM-BASED CARBENE CATALYSTS WITH CHELATING ALKYLIDENE LIGANDS

BACKGROUND OF THE INVENTION

The present invention relates to the preparation of ruthenium-based catalysts for metathesis, in particular to the synthesis of Ru-based metathesis catalysts, which comprise a chelating alkylidene ligand (so called "Hoveyda type" catalysts). The catalyst preparation method is based on a cross metathesis reaction in the presence of a polymer-supported cation exchange resin acting as a ligand scavenger. The method of the present invention is simple, straightforward, environmentally friendly and provides high yields.

Olefin metathesis is a fundamental catalytic reaction and one of the most versatile ways to make carbon-carbon bonds and build molecules. Various metathesis reaction pathways are known, such as ring-closing metathesis (RCM), ring-opening metathesis polymerization (ROMP), cross metathesis (CM) and their combinations. In the past years, olefin metathesis has become a widely used method for the formation of carbon-carbon bonds in organic synthesis and polymer chemistry. The development of well-defined ruthenium-based carbene catalysts by Schrock and Grubbs has led to a fast growth in the field of metathesis, particularly for industrial applications.

The Grubbs-type "first generation" catalyst, a ruthenium benzylidene complex with two tricyclohexylphosphine ligands, having the structure $(PCy_3)_2Cl_2Ru=CHPh$ (ref to Scheme 1; catalyst 1a was one of the first metathesis catalyst widely used in organic synthesis. It was followed by a more active "second generation" analog, in which N-heterocyclic carbene (NHC) ligands, such as "saturated" SIMes (=1,3-dimesityl-imidazolidine-2-ylidene) replaces one tricyclohexylphosphine ($PCy_3$) ligand (catalyst 1b).

Recently, the so-called "Hoveyda-type" catalysts are gaining increased importance. Hoveyda et al. disclosed latent metathesis catalysts based on a benzylidene-ether fragment connected to an alkylidene (carbene) moiety (ref to S. B. Garber, J. S. Kingsbury, B. L. Gray, A. H. Hoveyda, *J. Amer. Chem. Soc.* 2000, 122, 8168-8179) and WO 02/14376 A2. These type of Ru-catalysts comprise chelating alkylidene ligands (typically alkoxybenzylidene ligands) and either a $PCy_3$ ligand (first generation, catalyst 3a) or a NHC ligand (second generation, catalyst 3b). The cyclic benzylidene moiety and the chelating donor group may be further substituted.

The development of well-defined ruthenium catalysts has rendered olefin metathesis an efficient and reliable tool for the formation of carbon-carbon double bonds. The Grubbs-type catalysts 1a and 1b have found various applications in synthetic chemistry and the ruthenium indenylidene type catalysts 2a and 2b have proven to represent splendid alternatives. Hoveyda-type catalyst 3a and its phosphine-free congener 3b exhibit enhanced activity in various metathesis reactions compared to catalysts 1 and 2 and hold as a benchmark for further catalyst development.

Scheme 1

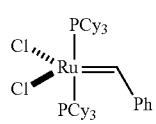
1a

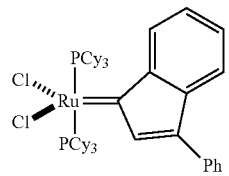
2a

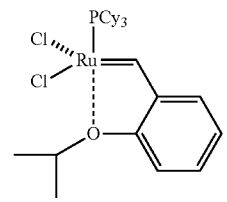
3a

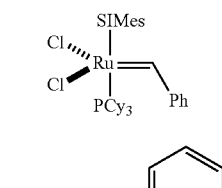
1b

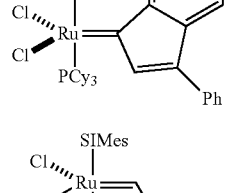
2b

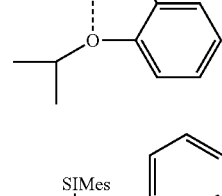
3b

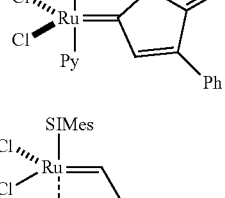
2c

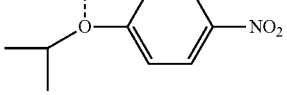
3c

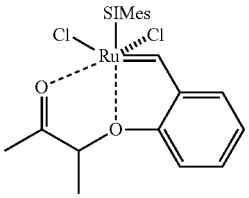
3d

Ru-indenylidene catalyst 2c was described recently by D. Burtscher, C. Lexer et al (ref to *J. of Polymer Science, Part A: Polymer Chemistry* 2008, Vol. 46, 4630-4635). Over the past years, Hoveyda-type catalysts with functional substituents at the aryl bridging group have been developed (ref to catalyst 3c). As an example, catalyst 3d, bearing a keto-group in the O-containing side chain, is described in WO 2008/034552.

The Hoveyda-type catalysts exhibit a broader application profile in metathesis reactions and allow to reduce the catalyst loading in some applications considerably. In some cases, these compounds can form latent catalyst species and are reported to be partially recyclable. Therefore, this type of catalysts is important for commercial applications. Consequently, appropriate catalyst manufacturing processes are required, which allow economical production in industrial scale.

The general preparation route for Hoveyda-type catalysts is based on the use of ruthenium carbene complexes of the type $X_2L_1L_2Ru=CHPh$ (wherein $L_1$ is a neutral 2-electron donor and $L_2$ preferably is a phosphine of the type $PPh_3$ or $PCy_3$) as starting complexes. These compounds are reacted with suitable styrenylether precursor ligands, which comprise an additional donor group. The new carbene bond is generated by cross metathesis reaction ("CM"), while one phosphine ligand is replaced by the donor group of the styrenylether ligand, thus forming a chelating ring complex.

More specifically, the Hoveyda-type catalysts 3a and 3b are generally prepared from reaction of 1a/b or 2a/b with 2-isopropoxystyrene in presence of copper(I)chloride (CuCl). In this reaction, CuCl acts as a phosphine scavenger, shifting the reaction towards closure of the $\kappa^2$-(C,O)-chelate. Unfortunately, CuCl is easily oxidized in presence of atmospheric oxygen which complicates handling during preparation of metathesis catalysts and during long-term storage. In addition, application of excess CuCl requires specific workup since it can not be quantitatively retained using column chromatography. Although alternative procedures have been reported in the literature, these methods require multiple preparative steps and/or post-end column chromatography.

S. Gessler, S. Randl and S. Blechert (*Tetrahedron Letters* 2000, 41, 9973-9976) report a 2-step procedure for preparation of catalyst 3b based on the exchange of $PCy_3$ by SIMes when starting from catalyst 3a. The product was purified by chromatography in 75% overall yield. Due to the multiple steps involved, this route is not commercially feasible.

A. Fuerstner, P. W. Davies and C. W. Lehmann (*Organometallics* 2005, 24, 4065-4071) report the preparation of bidentate ruthenium vinylcarbene catalysts derived from standard metathesis catalysts by enyne metathesis with phenylacetylene derivatives.

M. Bieniek, A. Michrowska, L. Gulajski and K. Grela (*Organometallics* 2007, 26, 1096-1099) describe a 2-step preparation method for the nitro-substituted Hoveyda-type catalyst 3c, using a metathesis exchange reaction.

S. Blechert et al. (*Synlett* 2001, 3, 430-432) report the use of a SIMes- and $PPh_3$-substituted Ru-indenylidene complex as a precursor for the preparation of catalyst 3b by cross metathesis with a phenylether. The product was purified by column chromatography. Yields of 40% are reported, thus this method seems not to be economical.

M. Barbasievicz et al. (*Organometallics* 2006, 25(15), 3599-3604) report the synthesis of chelating ruthenium quinoline and quinoxaline complexes starting from the Grubbs-type catalyst 1b (SIMes)($PCy_3$)$Cl_2Ru=CHPh$ and using Cu(I)Cl as phosphine scavenger.

WO 2004/112951 describes the preparation of ruthenium-based olefin metathesis catalysts by a cross metathesis reaction using Ru-indenylidene carbene complexes and an olefin. The preparation of Hoveyda-type catalysts comprising chelating alkylidenes is not disclosed.

U.S. Pat. No. 7,026,495 and US 2009/0088581 are related to chelating carbene ligand precursors for the preparation of olefin metathesis catalysts. Methods of preparing Hoveyda-type catalysts without the use of copper(I) chloride are disclosed. Organic acids, mineral acids (such as HCl), mild oxidants (such as bleach) or even water are employed. When employing gaseous HCl, yields of 82% for catalyst 3b are reported. Still, precipitation, separation and purification steps are needed in these methods. Furthermore, excess acid cannot be removed and thus remains in the reaction mixture.

In summary, despite considerable research in the field, the preparation methods for Hoveyda-type metathesis catalysts still suffer from various drawbacks. The synthesis routes starting from the Grubbs-type catalysts 1a and 1b usually employ hazardous chemicals, such as diazo reagents (e.g. diazoalkenes) for the preparation of the educt complex. Furthermore, precipitation, separation and purification steps (such as column chromatography etc) are needed in these methods. Finally, the yields and the purity of the resulting products need to be improved.

It was therefore an objective of the present invention to provide an improved process for preparation of ruthenium-based carbene catalysts with chelating alkylidene ligands ("Hoveyda-type" catalysts). The new method should not employ CuCl as a phosphine scavenger and should not require time-consuming isolation and/or purification steps. Furthermore, the method should provide the ruthenium carbene catalysts in high yields and high product purity (i.e. without residues of phosphine ligands, phosphine oxides or Cu ions). Finally, the method should be clean and simple, easily scalable, environmentally friendly, inexpensive and applicable to commercial, industrial scale.

SUMMARY OF THE INVENTION

According to the present invention, a ruthenium-based carbene catalysts with a chelating alkylidene ligand is prepared by reacting a ruthenium-alkylidene complex with an olefin derivative by a cross metathesis reaction in the presence of a polymer-supported cation exchange resin (herein abbreviated "PSR") according to equation (1):

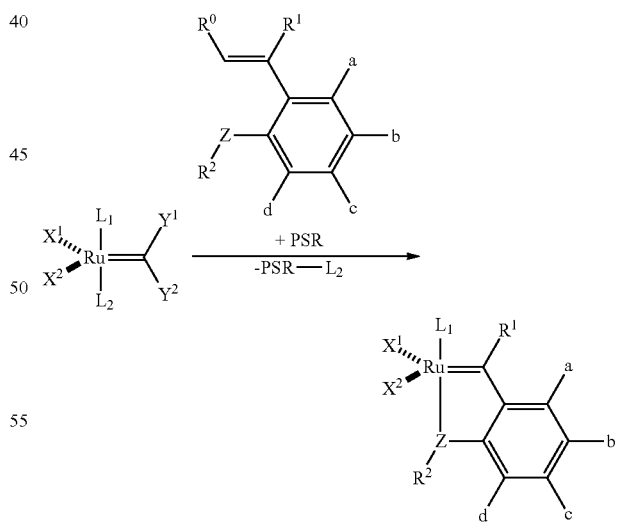

wherein
$L_1$ is a neutral 2-electron donor ligand,
$L_2$ is a neutral phosphine or amine ligand,
$X^1$ and $X^2$ are, independently from each other, inorganic or organic anionic ligands, such as halide anions, pseudohalide anions, hydroxides, acetates, trifluoracetates or carboxylates, $Y^1$ and $Y^2$ are, independently form each other, hydrogen, $C_1$-$C_6$-alkyl, $C_2$-$C_6$-alkenyl, $C_2$-$C_6$-alkynyl, $C_1$-$C_6$-alkylthio, phenyl, aryl, arylthio, $C_1$-$C_6$-alkylsulfonyl or $C_1$-$C_6$-alkylsulfinyl, or $Y^1$ and $Y^2$ are taken together to form a ring of the indenylidene type according to the formula

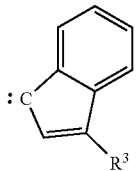

wherein in said formula $R^3$ is hydrogen or a substituted or unsubstituted phenyl group, $R^0$ and $R^1$ are, independently from each other, hydrogen, $C_1$-$C_{10}$-alkyl, $C_2$-$C_{10}$-alkenyl, $C_2$-$C_{10}$-alkynyl, a phenyl or an aryl group (which optionally can be substituted), a, b, c and d are, independent from each other, hydrogen, $C_1$-$C_{10}$-alkyl, $C_1$-$C_{10}$-alkoxy, $C_1$-$C_{10}$-alkylthio, $C_1$-$C_{10}$-silanyl, $C_1$-$C_{10}$-silyloxy, $C_2$-$C_{10}$-alkenyl, $C_2$-$C_{10}$-alkynyl, $C_6$-$C_{14}$-aryl, $C_6$-$C_{14}$-aryloxy, $C_6$-$C_{14}$-heterocyclic, $C_6$-$C_{14}$-heterocyclic aryl, phenyl, fluoro (—F), chloro (—Cl), bromo (—Br), iodo (—I), trifluormethyl (—CF$_3$), nitro (—NO$_2$), sulfinyl, sulfonyl, formyl, $C_1$-$C_{10}$-carbonyl, $C_1$-$C_{10}$-ester, $C_1$-$C_{10}$-aminocarbonyl, $C_1$-$C_{10}$-alkylamido, $C_1$-$C_{10}$-sulfonamido, $C_1$-$C_{10}$-uramido or $C_1$-$C_{10}$-aminosulfonyl with the provision that each of a, b, c or d can form a ring with each other, Z is a heterodonor atom such as oxygen (O) or sulphur (S) or a group comprising a heterodonor atom such as sulfinyl (>S=O), $R^2$ is a substituted or unsubstituted hydrocarbon group, such as alkyl, alkenyl, alkynyl, aryl, alkylamino, alkylthio, a substituted or unsubstituted keto group such as —C(R$^a$)$_2$—CO—C(R$^b$)$_3$, a substituted or unsubstituted ester group such as —C(R$^a$)$_2$—CO—O(R$^c$) (wherein in said groups R$^a$ is hydrogen or $C_1$-$C_{10}$-alkyl, R$^b$ is hydrogen, $C_1$-$C_{10}$-alkyl, $C_1$-$C_{10}$-fluoroalkyl, $C_1$-$C_{10}$-alkylamino, $C_1$-$C_{10}$-alkyl ammonium or $C_2$-$C_{10}$-alkenyl and R$^c$ is $C_1$-$C_{10}$-alkyl, $C_1$-$C_{10}$-fluoroalkyl, $C_1$-$C_{10}$-alkylamino, $C_1$-$C_{10}$-alkyl ammonium or $C_2$-$C_{10}$-alkenyl) with the provision that $R^2$ and/or Z may form a ring with d, PSR is a polymer-supported cation-exchange resin,
PSR-$L_2$ is the adduct of the polymer-supported cation-exchange resin with ligand $L_2$.

BRIEF DESCRIPTION OF THE FIGURE

FIG. 1: depicts the conversion of ruthenium indenylidene catalyst 2a to Hoveyda-type catalyst 3a in refluxing dichloromethane as a function of polymer-supported sulfonic acid resin (PSR) concentration and time.

DETAILED DESCRIPTION OF THE INVENTION

In a preferred embodiment of the method of the present invention, a ruthenium-based carbene catalysts with chelating alkylidene ligands is prepared by reacting a ruthenium-alkylidene complex with an olefin derivative by a cross metathesis reaction in the presence of a polymer-supported cation exchange resin ("PSR"), wherein $L_1$ is a phosphine ligand such as tricyclohexylphosphine, triphenylphosphine, cyclohexyl-phoban (=9-cyclohexyl-9-phosphabicyclononane), isobutyl-phoban (=9-isobutyl-9-phosphabicyclononane) or a saturated or unsaturated N-heterocyclic carbene (NHC) ligand, such as IMes (=1,3-dimesityl-imidazol-2-ylidene) or SIMes (=1,3-dimesityl-imidazolidine-2-ylidene), $L_2$ is a phosphine ligand such as tricyclohexylphosphine, triphenylphosphine, cyclohexyl-phobane or isobutylphobane or an amine ligand such as pyridine, 3-bromo-pyridine, 4-methyl pyridine, quinoline or piperidine, $X^1$ and $X^2$ are, independently form each other, chloride (Cl$^-$), bromide (Br$^-$), iodide (I$^-$), cyanide (CN$^-$) or acetate (AcO$^-$) ligands, $Y^1$ and $Y^2$ are, independently form each other, hydrogen, $C_1$-$C_6$-alkyl, $C_2$-$C_6$-alkenyl, phenyl, aryl, arylthio or $Y^1$ and $Y^2$ are taken together to form a ring of the indenylidene type wherein $R^3$ is a substituted or unsubstituted phenyl group, $R^0$ and $R^1$ are, independently from each other, hydrogen, $C_1$-$C_{10}$-alkyl, $C_2$-$C_{10}$-alkenyl, a phenyl or an aryl group, a, b, c, and d are, independently from each other, hydrogen, phenyl, fluoro (—F), chloro (—Cl), nitro (—NO$_2$), trifluormethyl (—CF$_3$), acetamido (—N(H)—CO—CH$_3$), trifluoracetamido (—N(H)—CO—CF$_3$), difluorchloracetamido (—N(H)—CO—CClF$_2$), pentafluorbenzamido (—N(H)—CO—C$_6$F$_5$), p-nitro-benzamido (—N(H)—CO—C$_6$H$_4$—NO$_2$), dimethylamidosulfonyl (—SO$_2$—N(CH$_3$)$_2$), ethylsulfonyl (—SO$_2$—C$_2$H$_5$), ethylester (—O—CO—C$_2$H$_5$) or formyl (—CHO), Z is a heterodonor atom such as oxygen (O) or sulphur (S), $R^2$ is a substituted or unsubstituted alkyl group such as —CH$_3$ or —CH(CH$_3$)$_2$, a substituted or unsubstituted keto group such as —CH$_2$—CO—CH$_3$, —CH$_2$—CO—C$_2$H$_5$, —CH(CH$_3$)—CO—CH$_3$ or —CH(CH$_3$)—CO—C$_2$H$_5$, a substituted or unsubstituted ester group such as —CH$_2$—CO—O—CH$_3$, —CH$_2$—CO—O—C$_2$H$_5$, —CH(CH$_3$)—CO—O—CH$_3$ or —CH(CH$_3$)—CO—O—C$_2$H$_5$ or an amino group containing ester group such as —CH(CH$_3$)—CO—O—C$_2$H$_4$—N(CH$_3$)$_2$, PSR is a polymer-supported cation-exchange resin and
PSR-$L_2$ is the adduct of the polymer-supported cation-exchange resin with ligand $L_2$.

The process may further comprise the step of removing the adduct of ligand $L_2$ with the polymer-supported cation-exchange resin (=PSR-$L_2$) from the reaction mixture.

The process is conducted in suitable organic solvents. It may further comprise the steps of removing the solvent(s) from the reaction mixture after reaction (for example by evaporating in vacuo), suspending the remaining residues in a non-polar hydrocarbon solvent and separating the precipitated product (for example by filtration). In addition, the process may further comprise additional product purification and drying steps well known to the person skilled in the art. By the method of the present invention, generally very good yields in the range of >90% are obtained.

As a major advantage, the process of the present invention avoids the use of Cu(I)Cl. This compound is widely used as phosphine scavenger and accelerates the conversion of the Ru alkylidene starting complex by lowering the free concentration of ligand $L_2$ (preferably a phosphine or amine ligand) in solution and prevents the coordination of ligand $L_2$ to the target ruthenium catalyst. Circumventing the application of CuCl consequently demands an efficient ligand (in particular phosphine or amine) scavenging reagent.

A. Falchi and M. Taddei (ref to *Organic Letters* 2000, 2, 3429-3431) reported the use of PEG-dichlorotriazine as a soluble polymer-supported scavenger for alcohols, thiols, phosphines and phosphine oxides. Although its activity as a phosphine scavenger was evidenced from its successful application in the workup, however the necessity for additional steps for preparation of the scavenger polymer limits its applicability.

On the other hand, polymer-supported cation exchange resins (PSR) were applied in acidic form for the removal of tertiary amines from the reaction mixture after "Pfitzner-Moffatt" oxidation, the subsequent removal of the resin allows the isolation of the corresponding ketones in high yield (ref to D. L. Flynn, J. Z. Crich, R. V. Devraj, S. L. Hockerman, J. J. Parlow, M. S. South and S. Woodard, *Journal of the American Chemical Society* 1997, 119, 4874-4881).

Furthermore, polymer-supported cation-exchange resins are used for removal of phosphine traces from liquid higher olefins in petrochemical applications (ref to EP 271 143B1). Herein, the polymer-supported cation exchange resins (PSR) do not act as a reaction partner.

Surprisingly, it was found by the present inventors that suitable polymer-supported resins, specifically polymer-supported cation exchange resins (hereinafter abbreviated "PSR") are successfully employed for the removal of ligand $L_2$ in the reaction according to equation (1).

Preferably, the polymer-supported cation-exchange resins comprise acidic groups such as sulfonic acid groups (—$SO_3H$). An example for this PSR type is AMBERLYST 15A (available from Rohm and Haas Co or Aldrich Chemicals). This material is a strongly acidic, cross-linked polystyrene-divinylbenzene-polymer with sulfonic acid groups, available as macroreticular spherical beads. Similar products are manufactured by other suppliers.

Furthermore, polymer-supported resins (PSR) with other acidic groups, such as carboxylic acid groups (—COOH) or phosphoric acid groups may be employed. Examples for suitable polymer-supported carboxylic acids are "PL-Mal resin" and "PL-MeMal resin", both available from Varian Polymer Laboratories (Darmstadt, Germany).

Still further, polymer-supported resins (PSR) with acid chloride groups, such as polymer-supported sulfonylchloride (—$SO_2Cl$), polymer-supported acetylchloride (—COCl) or polymer-supported tosylchloride may be used in the process of the present invention. An example for a suitable polymer-supported sulfonylchloride resin is "PL-$SO_2Cl$ resin", available from Varian Polymer Laboratories (Darmstadt, Germany). Similar products are sold by other vendors.

When added in at least stoichiometric amounts, the PSR compounds lead to significant improvement in yield, as they are shifting the reaction in the direction of closure of the $\kappa^2$-(C,O)-chelate. Thus, stable intermediate products or transition compounds are not formed in the reaction. Consequently the method of the present invention leads to high purity catalyst and yields in the range of >90%.

After the reaction, the PSR-$L_2$ adduct is easily removed from the reaction mixture. As there is a heterogeneous system, no acidic compounds remain. The ligand adduct (PSR-$L_2$) can be straightforwardly reactivated after use, bringing about a recovery of valuable $L_2$ ligands, e.g. expensive phosphine ligands. Standard operating procedures for the regeneration of ion exchange resins may be employed (such as acid washing etc). Therefore the process of the present invention is economical, sustainable and environmentally friendly.

The quantities of polymer-supported cation-exchange resin (PSR) added in relation to the starting Ru(II)-alkylidene complex are in the range of 1 to 15 equivalents, preferably in the range of 2 to 10 equivalents and particularly preferably in the range of 4 to 8 equivalents. It was found that the use of 4 to 8 equivalents of PSR is particularly advantageous, as very short reaction times of less than 1 hour can be obtained in the process (ref to Comparative Example).

Generally, Ru(II)-alkylidene complexes of the type $(L_1)(L_2)X^1X^2Ru=CY^1Y^2$ are used as starting compounds in the method of the present invention. Preferably, penta-coordinated ruthenium benzylidene or indenylidene carbene complexes are employed, with indenylidene complexes being particularly preferred. Herein, ligand $L_1$ generally is a neutral 2-electron donor ligand, preferably a phosphine ligand or a saturated or unsaturated N-heterocyclic carbene (NHC) ligand. Examples for suitable NHC ligands ("N-heterocyclic carbene" ligands) are saturated SIMes (=1,3-dimesityl-imidazolidine-2-ylidene), saturated SIPr (=1,3-bis-(2,6-diisopropylphenyl)-imidazolidine-2-ylidene) or unsaturated IMes (=1,3-dimesityl-imidazole-2-ylidene).

$X^1$ and $X^2$ are, independently from each other, inorganic or organic anionic (i.e. negatively charged) ligands, such as halide anions, pseudohalide anions, hydroxides, acetates, trifluoracetates or carboxylates. Examples for suitable anionic ligands X are the halides, with $Cl^-$ being most preferred.

The precursors for the chelating alkylidene ligands (herein called "olefin derivative") have the following general formula:

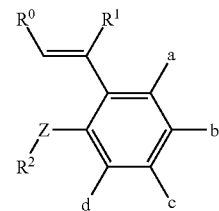

In this formula, the substituents $R^0$, $R^1$, $R^2$, a, b, c, d and the heterodonor atom Z have the meaning as given above.

In general, the precursor ligands may be prepared according to standard procedures known from the literature or may be obtained commercially from various suppliers. Examples of olefin derivatives suitable for the method of the present invention are (E/Z)-1-Isopropoxy-2-(1-propenyl)-benzene ("isopropoxystyrene"), (E/Z)-1-[2-(1-propen-1-yl)-phenoxy]-2-propanone), 2-isoprop-oxy-4-nitro-styrene or 2-isopropoxy-3-vinyl-biphenyl. A further suitable olefine derivative is 3-(2-(prop-1-enyl)phenoxy)-butan-2-one.

The starting Ru(II)-alkylidene complex is dissolved in the appropriate solvent and the ligand precursor (olefin derivative) is added. The molar ratio of olefin ligand precursor vs. Ru-starting complex is in the range of 1 to 1.5 equivalents, preferably in the range of 1 to 1.2 equivalents. However, higher or lower amounts may be added.

Various organic solvents may be used in the preparation process of the present invention. Preferably, the process is conducted in chlorinated hydrocarbon solvents such as dichloromethane (DCM), chloroform or 1,2-dichloroethane (DCE) or in cyclic ethers such as tetrahydrofurane (THF) or dioxane. However, aromatic hydrocarbon solvents such as benzene or toluene as well as esters and mixtures of the listed solvents may be employed.

The reaction temperatures are in the range of 0° C. to 120° C., preferably in the range of 20° C. to 100° C. The suitable reaction times depend on the type of olefin derivative and quantity of PSR employed. Typically, the reaction times are in the range from 0.5 to 4 hours, preferably in the range from 0.5 to 2 hours.

After stirring the reaction mixture for a given period of time, the reacted PSR material (=adduct PSR-L$_2$) is removed by a standard separation process, such as filtration (e.g. with filter paper, glass frit, cotton plug) and/or by decantation, centrifuge or filter dryer. Thereafter, the solvent(s) are reduced or removed, for example by evaporation in vacuo. The remaining residue is then suspended in a suitable non-polar hydrocarbon solvent (such as n-pentane, n-hexane, n-heptane and/or cyclohexane or mixtures thereof), whereby the catalyst product is precipitating. Depending on the catalyst product made, low aliphatic alcohols (e.g. methanol) may also be used as solvents for suspension.

After separation of the precipitate (e.g. by filtration) the final product may be dried (in vacuo, or in a drying oven etc). Additional washing and/or drying steps may be conducted. Due to the high purity of the resulting catalyst products, there is basically no need for further purification steps. However, if necessary, additional purification steps such as column chromatography (LC, HPLC etc) or recrystallisation may be performed.

As already outlined, the process of the present invention leads to products in high yields (generally in the range of >90%). Typically, the Cu-content of the Ru catalyst products obtained according to the process is less than 10 ppm, preferably less than 5 ppm (as determined by ICP; ICP=inductive coupled plasma).

The preparation process according to the present invention is very versatile and useful for industrial, large scale production of catalysts and can be applied to the manufacturing of a great variety of Ru-based Hoveyda-type catalysts. These catalyst products find use in various of metathesis reactions, for example in ring-closing metathesis (RCM), ring-opening metathesis polymerization (ROMP), cross metathesis (CM), acyclic dien-metathesis-polymerisation (ADMET) and/or their combinations.

The following examples may further describe the invention without limiting the scope of protection.

EXAMPLE 1

Preparation of Hoveyda-Type Catalyst 3a from 2a

A flame-dried Schlenk reaction flask is charged with a stir bar and put under an Ar atmosphere. 923 mg [Dichloro-(3-phenyl-1H-inden-1-ylidene)-bis-(tricyclohexyl-phosphine)-ruthenium(II)] 2a (1.0 mmol; Umicore AG & Co KG, Hanau), 173 mg 2-isopropoxystyrene (1.05 mmol; 1.05 equiv.; Aldrich) and 1026 mg Amberlyst 15-A resin in dry form (4.0 mmol, 4 equiv.; Rohm and Haas Co., Philadelphia, USA) are loaded into the reaction flask and 25 mL dichloromethane (DCM) is added. The reaction is stirred at 40° C. for 75 minutes and the solution colored from red to brown. Subsequently, the reaction mixture is sent through a Pasteur pipette equipped with a cotton plug to remove the Amberlyst resin. Evaporation of all volatiles, suspending the residue in 20 mL n-hexane and subsequent filtration and drying of the precipitate in vacuo afforded 548 mg of the desired compound 3a (yield: 91%)

EXAMPLE 2

Preparation of Hoveyda-Type Catalyst 3b from 2b

A flame-dried Schlenk reaction flask is charged with a stir bar and put under an Ar atmosphere. 949 mg [Dichloro-(3-phenyl-1H-inden-1-yliden)-(1,3-dimesityl-4,5-dihydro-imidazol-2-ylidene)-(tricyclohexylphosphine)-ruthenium(II)] 2b (1.0 mmol; Umicore AG & Co KG, Hanau), 173 mg 2-isopropoxystyrene (1.05 mmol; 1.05 equiv.) and 1026 mg Amberlyst 15-A resin in dry form (4.0 mmol; 4 equiv) was loaded into the reaction flask and 25 mL THF is added. The reaction is stirred at 68° C. for 1 hour, during which the reaction mixture colors from red to green. Then, the reaction mixture is sent through a Pasteur pipette equipped with a cotton plug to remove the Amberlyst resin. Evaporation of all volatiles, suspending the residue in 20 mL n-hexane and subsequent filtration and drying of the precipitate in vacuo afforded 576 mg of the desired compound as a green, air-stable product (yield: 94%). The $^1$H and $^{13}$C NMR spectral data of the dried greenish powder were in accordance to literature reports.

EXAMPLE 3

Preparation of Hoveyda-Type Catalyst 3b from 1b

A flame-dried Schlenk reaction flask is charged with a stir bar and put under an Ar atmosphere. 849 mg 1b (1.00 mmol), 173 mg 2-isopropoxystyrene (1.05 mmol; 1.05 equiv) and 1026 mg Amberlyst 15-A resin in dry form (4.00 mmol; 4 equiv) was loaded into the reaction flask and 25 mL THF is added. The reaction was stirred at 40° C. for 1.5 hour, during which the reaction mixture colors from pink to green. Then, the reaction mixture is sent through a Pasteur pipette equipped with a cotton plug to remove the polystyrene sulfonic acid resin. Evaporation of all volatiles, suspending in 20 mL hexane and subsequent filtration and drying in vacuo afforded the desired compound 3b as a green air-stable product. $^1$H and $^{13}$C NMR analyses are in agreement with those found in literature.

EXAMPLE 4

Preparation of Hoveyda-Type Catalyst 3c from 2b

A flame-dried Schlenk reaction flask is charged with a stir bar and put under Ar atmosphere. 475 mg Dichloro-(3-phenyl-1H-inden-1-yliden)-(1,3-dimesityl-4,5-dihydro-imidazol-2-ylidene)-(tricyclohexylphosphine)-ruthenium(II)] 2b (0.50 mmol, 1.00 equiv; Umicore AG & Co KG, Hanau), 117 mg 2-isopropoxy-4-nitro-styrene (0.52 mmol; 1.05 equiv) and 500.7 mg of Amberlyst 15-A resin (2.0 mmol; 4.00 equiv) are added. 15 mL anhydrous THF is added and the mixture is stirred at 70° C. The reaction is monitored by $^{31}$P NMR spectroscopy of the reaction mixture every hour.

Within 2 hours, the signal of the starting compound completely disappears and the reaction mixture colors from red to green. At this point, the reaction mixture is allowed to cool down to room temperature and the polymer resin is filtered off on a Pasteur pipette equipped with a cotton plug. The filtrate is concentrated in vacuo and suspended in 10 mL n-hexane. The product is filtered off on a glass frit. Additionally, the filtrate is concentrated in vacuo, suspended in n-hexane and filtered on a P4 glass frit as a green product. Thoroughly washing of the green product (3×5 mL n-pentane) and subsequent drying of the green product yields 458 mg of the desired compound 3c (91%).

EXAMPLE 5

Preparation of Hoveyda-Type Catalyst 3d from 2b

A flame-dried Schlenk reaction flask is charged with a stir bar and put under Ar atmosphere. 475 mg [Dichloro-(3-phenyl-1H-inden-1-yliden)-(1,3-dimesityl-4,5-dihydro-imidazol-2-ylidene)-(tricyclohexylphosphine)-ruthenium(II)] 2b (0.50 mmol, 1.00 equiv; Umicore AG & Co KG, Hanau), 100 mg 3-(2-(prop-1-enyl)phenoxy)-butan-2-one (0.52 mmol; 1.05 equiv) and 500 mg of the polymer-supported Amberlyst 15-A resin (2.0 mmol; 4.00 equiv) are added. 15 mL anhydrous THF is added and the mixture is stirred at 70° C. The reaction is monitored by $^{31}$P NMR spectroscopy of the reaction mixture every hour.

Within 4 hours of reflux, the reaction mixture turns from red to dark green color. The $^{31}$P NMR spectrum from the reaction mixture after 4 hours refluxing does not reveal a signal from the starting compound. At this point, the reaction mixture is allowed to cool down to room temperature and the polymer resin is filtered off on a Pasteur pipette equipped with a cotton plug. The filtrate is concentrated in vacuo and suspended in 10 mL n-hexane. The product is filtered off on a glass frit. Additionally, the filtrate is concentrated in vacuo, suspended in n-hexane and filtered on a P4 glass frit as a green product. Thoroughly washing of the green product (3×5 mL n-pentane) and subsequent drying of the green product yields the desired compound 3d in very good yield.

EXAMPLE 6

Preparation of Hoveyda-Type Catalyst 3b from 2c

A flame-dried Schlenk reaction ask is charged with a stir bar and put under an Ar atmosphere. 748 mg [Dichloro-(3-phenyl-1H-inden-1-yliden)-(1,3-dimesityl-4,5-dihydro-imidazol-2-ylidene)-(pyridine)-ruthenium(II)] 2c (1.00 mmol, Umicore AG & Co KG, Hanau), 173 mg 2-isopropoxystyrene (1.05 mmol; 1.05 equiv) and 1026 mg Amberlyst 15-A resin (4.00 mmol; 4 equiv) is loaded into the reaction ask and 25 mL THF is added. The reaction mixture is stirred at 40° C. for 1 hour, during which the reaction mixture turns from red to green color. Then, the reaction mixture is sent through a Pasteur pipette equipped with a cotton plug to remove the polystyrene sulfonic acid resin. Evaporation of all volatiles, suspending in 20 mL n-hexane and subsequent filtration and drying in vacuo afforded 578 mg of the desired compound 3b as a green, air-stable product (yield: 94%). $^1$H and $^{13}$C NMR analytics are in agreement with those found in literature.

COMPARATIVE EXAMPLE

In a comparative example, the potential of the polymer-supported ion exchange resin (in this case Amberlyst 15-A) as an in situ phosphine scavenger reagent was investigated. For comparative purposes, the reaction is also conducted without the addition of PSR material.

The reaction towards the synthesis of Hoveyda-type catalyst 3a upon reaction of ruthenium indenylidene complex 2a with 1.05 equiv 2-isopropoxystyrene was conducted. Progress of the reaction of 2a to 3a in dichloromethane (DCM) ($c_{Ru}$=0.01 M) at 40° C. in presence of various amounts of Amberlyst 15-A resin was conveniently monitored by $^{31}$P NMR analysis of the crude reaction mixtures at selected time intervals. The results are depicted in FIG. 1, which documents the conversion of ruthenium indenylidene catalyst 2a to Hoveyda-type catalyst 3a in refluxing dichloromethane as a function of polymer-supported sulfonic acid resin (PSR) concentration and time. FIG. 1 clearly demonstrates the impact of the PSR on the proceeding of the reaction. In absence of Amberlyst 15-A resin, merely 23% of starting material is consumed after 2 hours. Due to the lack of the phosphine scavenging agent, the Hoveyda-type catalyst 3a is present as its bis-phosphine adduct 3a.PCy$_3$ ($\delta$ 36.3 ppm; monitored by $^{31}$P NMR). Upon raising the amount of Amberlyst 15-A to 1 or 2 equiv, modest improvement of the reaction rate is observed. However, application of 4 to 8 equiv of PSR affords clean conversion of complex 2a to 3a within 1 hour.

What is claimed is:

1. A process for preparation of ruthenium-based carbene catalysts with chelating alkylidene ligands by reacting a ruthenium-alkylidene complex with an olefin derivative in a cross metathesis reaction in the presence of a polymer-supported cation exchange resin (PSR) according to equation:

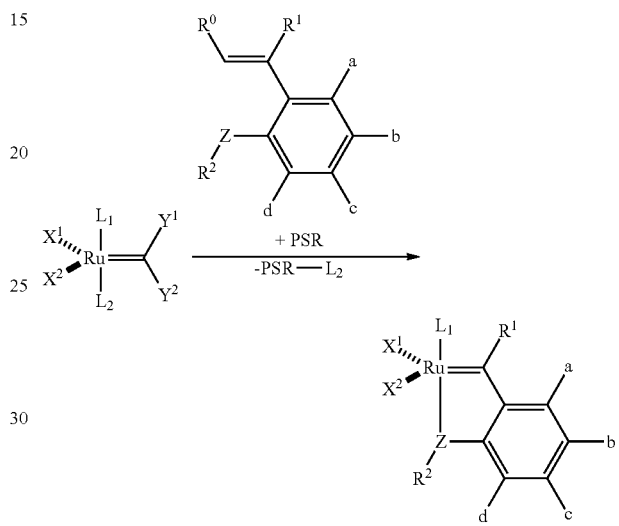

wherein
  $L_1$ is a neutral 2-electron donor ligand,
  $L_2$ is a neutral amine or phosphine ligand,
  $X^1$ and $X^2$ are, independently from each other, inorganic or organic anionic ligands, such as halide anions, pseudohalide anions, hydroxides, acetates, trifluoracetates or carboxylates,
  $Y_1$ and $Y_2$ are, independently from each other, hydrogen, $C_1$-$C_6$-alkyl, $C_2$-$C_6$-alkenyl, $C_2$-$C_6$-alkynyl, $C_1$-$C_6$-alkylthio, phenyl, aryl, arylthio, $C_1$-$C_6$-alkylsulfonyl or $C_1$-$C_6$-alkylsulfinyl, or $Y^1$ and $Y^2$ are taken together to form a ring of the indenylidene type according to the formula

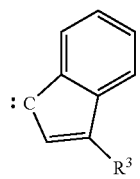

wherein in said formula $R^3$ is hydrogen or a substituted or unsubstituted phenyl group,
  $R^0$ and $R^1$ are, independently from each other, hydrogen, $C_1$-$C_{10}$-alkyl, $C_2$-$C_{10}$-alkenyl, $C_2$-$C_{10}$-alkynyl, a phenyl or an aryl group (which optionally can be substituted),
  a, b, c and d are, independently from each other, hydrogen, $C_1$-$C_{10}$-alkyl, $C_1$-$C_{10}$-alkoxy, $C_1$-$C_{10}$-alkylthio, $C_1$-$C_{10}$-silanyl, $C_1$-$C_{10}$-silyloxy, $C_2$-$C_{10}$-alkenyl, $C_2$-$C_{10}$-alkynyl, $C_6$-$C_{14}$-aryl, $C_6$-$C_{14}$-aryloxy, $C_6$-$C_{14}$-heterocyclic, $C_6$-$C_{14}$-heterocyclic aryl, phenyl, fluoro (—F), chloro (—Cl), bromo (—Br), iodo (—I), trifluormethyl (—$CF_3$), nitro (—$NO_2$), sulfinyl, sulfonyl, formyl, $C_1$-$C_{10}$-carbonyl, $C_1$-$C_{10}$-ester, $C_1$-$C_{10}$-aminocarbonyl, $C_1$-$C_{10}$-alkylamido, $C_1$-$C_{10}$-sulfonamido, $C_1$-$C_{10}$-uramido, $C_1$-$C_{10}$-aminosulfonyl, and ionic groups such as —$[C_5H_6]^+ PF_6^-$ or —$[N(C_2H_5)_2CH_3]^+ Cl^-$, with the provision that each of a, b, c or d can form a ring with each other, Z is a heterodonor atom such as oxygen (O) or sulphur (S) or a group comprising a heterodonor atom such as sulfinyl (>S=O), $R^2$ is a substituted or unsubstituted hydrocarbon group, such as alkyl, alkenyl, alkynyl, aryl, alkylamino, alkylthio, a substituted or unsubstituted keto group such as —$C(R^a)_2$—CO—$C(R^b)_3$, a substituted or unsubstituted ester group such as —$C(R^a)_2$—CO—$O(R^c)$ (wherein in said groups $R^a$ is hydrogen or $C_1$-$C_{10}$-alkyl, $R^b$ is hydrogen, $C_1$-$C_{10}$-alkyl, $C_1$-$C_{10}$-fluoroalkyl, $C_1$-$C_{10}$-alkylamino, $C_1$-$C_{10}$-alkyl ammonium or $C_2$-$C_{10}$-alkenyl and $R^c$ is $C_1$-$C_{10}$-alkyl, $C_1$-$C_{10}$-fluoroalkyl, $C_1$-$C_{10}$-alkylamino, $C_1$-$C_{10}$-alkyl ammonium or $C_2$-$C_{10}$-alkenyl) with the provision that $R^2$ and/or Z may form a ring with d, PSR is a polymer-supported cation-exchange resin and PSR-$L_2$ is the adduct of the polymer-supported cation-exchange resin with ligand $L_2$.

2. Process according to claim 1, further comprising the separation of the adduct of the polymer-supported cation-exchange resin with ligand $L_2$ (PSR-$L_2$) from the reaction mixture.

3. Process according to claim 1, wherein the ruthenium-alkylidene complex is a ruthenium-indenylidene complex, in which $Y^1$ and $Y^2$ are taken together to form a ring of the indenylidene type.

4. Process according to claim 1, wherein the ruthenium-alkylidene complex is a ruthenium-benzylidene complex.

5. Process according to claim 1, wherein the polymer-supported cation-exchange resin (PSR) is an acidic resin and comprises sulfonic acid (—$SO_3H$) or carboxylic acid (—COOH) groups.

6. Process according to claim 1, wherein the polymer-supported cation-exchange resin (PSR) comprises sulfonylchloride (—$SO_2Cl$) groups or carboxylic acid chloride (—COCl) groups.

7. Process according to claim 1, wherein the polymer-supported cation-exchange resin (PSR) is added in quantities in the range of 2 to 15 equivalents, preferably in the range of 2 to 10 equivalents (based on the starting Ru alkylidene complex).

8. Process according to claim 1, wherein the olefin derivative is added in quantities in the range of 1 to 1.5 equivalents, preferably in the range of 1 to 1.2 equivalents (based on the starting Ru alkylidene complex).

9. Process according to claim 1, wherein the olefin derivative is selected from the group of (E/Z)-1-Isopropoxy-2-(1-propenyl)-benzene ("isopropoxystyrene"), (E/Z)-1-[2-(1-propen-1-yl)-phenoxy]-2-propanone, 2-isoprop-oxy-4-nitro-styrene or 2-isopropoxy-3-vinyl-biphenyl.

10. Process according to claim 1, wherein the reaction is conducted in an organic solvent selected from the group consisting of chlorinated hydrocarbons, aromatic hydrocarbons, cyclic ethers, esters, and mixtures thereof.

11. Process according to claim 1, wherein the reaction temperature is in the range of 20 to 120° C., preferably in the range of 20 to 100° C.

12. Process according to claim 1, wherein the reaction time is in the range of 0.5 to 4 hours, preferably in the range of 0.5 to 2 hours.

13. Process according to claim 1, further comprising the steps of
removing the solvent(s) from the reaction mixture after reaction,
suspending the remaining residues in a non-polar hydrocarbon solvent, and
separating the precipitated catalyst product.

14. Process according to claim 13, further comprising the step of drying the precipitated catalyst product.

* * * * *